United States Patent [19]

Gilula

[11] 4,069,813

[45] Jan. 24, 1978

[54] METHOD AND APPARATUS FOR APPLYING STRESS FOR KNEE ARTHROGRAPHY AND THE LIKE

[75] Inventor: Louis A. Gilula, St. Louis, Mo.

[73] Assignee: Jean Y. Barbier, St. Louis, Mo.; a part interest

[21] Appl. No.: 735,189

[22] Filed: Oct. 26, 1976

[51] Int. Cl.² ............................................. A61B 5/00
[52] U.S. Cl. ................................. 128/2 R; 128/133; 128/DIG. 15
[58] Field of Search ........ 128/2 R, 133, 134, DIG. 15

[56] References Cited

U.S. PATENT DOCUMENTS

| 3,297,026 | 1/1967 | Van Pelt | 128/133 |
| 3,535,718 | 10/1970 | Murcott | 128/133 X R |
| 3,640,273 | 2/1972 | Ray | 128/133 |
| 3,939,829 | 2/1976 | Spann | 128/133 |

*Primary Examiner*—Lawrence W. Trapp

[57] ABSTRACT

For use chiefly in arthrography, a strap is looped about the limb above the joint (for example, the knee) to be studied; and the strap loop is adjusted so that an edge grasping member, slide-mounted on the strap, will reach to either edge of the fluoroscopic table. To study the medial side of the joint, the strap loop is extended to the corresponding side of the table edge and hooked over it; then the operator applies a force to the limb below the joint in the direction opposite to that of the strap. So applying stress opens the medial side of the joint, so as to present for radiographic study its cartilages and the menisci between them. To study the lateral side of the joint, the process is reversed. The preferred apparatus used employs an edge-grasping member formed as a double hook, so that when the side toward which the loop is directed is reversed and the edge-grasping members slid along it to grasp the other edge of the fluoroscopic table, the second side of the joint may be studied without moving the loop position relative to the patient's limb and without twisting the strap.

8 Claims, 1 Drawing Figure

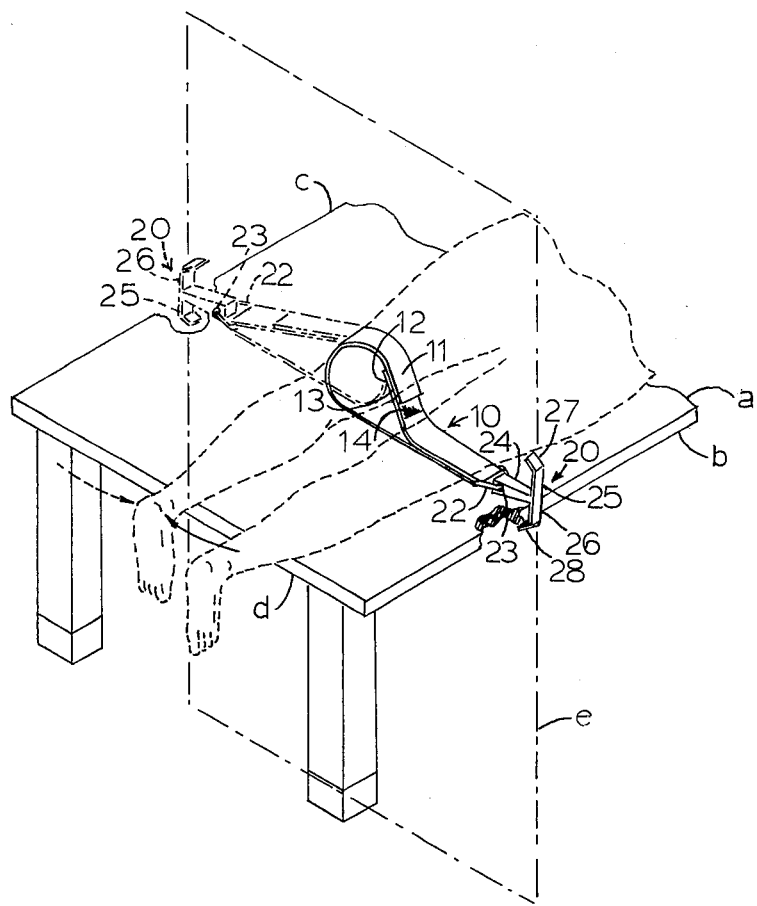

METHOD AND APPARATUS FOR APPLYING STRESS FOR KNEE ARTHROGRAPHY AND THE LIKE

BACKGROUND OF THE INVENTION

The present invention relates to a method of widening the spaces at the medial and lateral sides of a limb joint, in particular the knee joint, for studying these sides alternately. It has particular application to applying effective valgus and varus stress in the making of air contrast knee arthrograms. Apparatus is provided to loop about the limb above the joint, and to extend to grasp the side edges of the study table alternately without removal from or repositioning the limb.

The alternate application of valgus and varus stress is a familiar procedure in making such arthrograms. When a radiographic contrast agent is injected into the joint, the widening of the joints spaces will effect definition of the femoral and tibial cartilages, and of the menisci between them.

To apply such stress to the knee, for example, a force or restraint directed to one side must be applied above the knee and the operator must apply a force below the knee directed toward the opposite side. To attempt to apply such stress without apparatus, by having a technologist apply a force in one direction above the knee while a force in the other direction is applied below the knee, sacrifices full control and may expose the technologist to unnecessary radiation. In order to overcome these difficulties, restraints, typically made of curved sheet metal, have been secured to the examining table at a position somewhat above the knee of the patient, so that the operator could apply a distal force, conventionally at the ankle, in the opposite direction, that is directed either medially or laterally. The use of such metal restraints is at best difficult; and their use is precluded when the leg must be elevated substantially off the table, as well as when patients have very large thighs.

Since the use of such a device is a matter of choice with the arthrographer, restraint devices which must be fixed to the fluoroscopic table are undesirable. Especially for an arthrographer who may work at more than one hospital or clinic, it is desirable that restraint apparatus be readily removable from the fluoroscopic table and preferably be portable.

SUMMARY OF THE INVENTION

The method of the present invention may be summarized as consisting of the steps of positioning the limb, whose joint is to be studied, on a study table with one side of the limb nearer to one edge of the table and the other side of the limb nearer to its other edge, and looping about the limb, at a position above the joint, a strap having a sliding hook member, so adjusting its loop length that the hook member may grasp either table edge. For widening the joint spaces and studying the medial and lateral sides of the joint alternately, the strap is extended toward that edge of the table nearer to the side of the joint to be first studied, and that edge is grasped with the hook member; then a force, in the direction opposite to the extension of the loop, is applied to the limb distal to the joint. After study of that side of the joint in whose direction the loop extends, the force applied below the joint is released, as in the grasp of the hook member. Then for studying the opposite side, the operator extends the strap loop toward the opposite edge of the table, grasps it with the hook member, and applies to the limb distal to the joint a force in the direction opposite that to which the strap loop extends, providing sufficient stress to permit study of that side of the joint. After such study the force so applied is released, as is the hook member, and the strap loop is removed.

The apparatus of the present invention includes strap means to form an adjustable length loop sufficient to surround such limb when in centered position on the table and extend toward either side edge thereof, and means to grasp either such edge without twisting the loop strap. In the preferred apparatus, the grasping means is a grapple-like member having a stem portion and two hook portions extending in opposite directions from one end of the stem portion, these hook portions defining a grapple hook plane. The opposite end of the stem portion has link means to mount the looped strap substantially perpendicular to such grapple hook plane.

BRIEF DESCRIPTION OF THE DRAWING

The drawing is a schematic view of the lower end portion of a fluoroscopic table on which a patient may be positioned as shown in dashed lines. The strap and grapple hook apparatus shown in solid lines depict it in position to apply stress to the knee joint of the patient when a lateral-directed force is applied by an operator at the ankle, as shown by the solid arrow. The phantom lines show the apparatus in position to apply stress to the knee joint when a medial-directed force is applied at the ankle, as shown by the phantom arrow.

DESCRIPTION OF THE PREFERRED EMBODIMENT

Referring to the drawing, a conventional fluoroscopic table designated $a$ is utilized; only its lower end is illustrated. The dashed lines indicate a patient in position on the table for making arthrograms of his left knee; the patient is illustrated lying face down with the left knee approximately centered between the table right edge $b$ and left edge $c$. The patient's feet may hang over the table edge $d$. An X-ray source, not shown, is to be positioned directly below the patient's left knee joint, while a radiographic plate, not shown, is positioned in a holder above the surface of the table $a$.

The apparatus of the present invention includes a flexible strap generally designated 10, preferably formed of a suitable conventional fabric material, adapted to be fastened in a loop by the engagement of overlapped end portions 11, 12 whose end faces 13, 14 are covered with that type of complementary self-engaging hook-and-loop material of the type known by the trademark VELCRO. Sufficient length is provided so that when the strap 10 is looped about the lower thigh of a patient, the end faces 13, 14 engaged to each other, and the strap drawn toward either of the edges $b$, $c$ of the table $a$, either said edge may be graspingly engaged by a grasping member generally designated 20 which is mounted to the strap by the sliding link 22.

As seen in the drawings, the link 22 may be formed of heavy bent wire or rod to a trapezoidal shape whose broader side is of sufficient width to accommodate the strap 10. Its narrower side passes through a bore 23 in the broader end of a tapering stem portion 24 of the grasping member 20. From the opposite end of the stem portion 24 extend two hook portions 25, 26, each being of sufficient width to grasp the table edges $b$, $c$. These extend in directions opposite each other substantially perpendicular to the stem portion 24. In so extending opposite to each other they define a grapple hook plane *e* shown in phantom lines. The hook portions 25, 26 terminate in reverse turned ends 27, 28 which extend therefrom at obtuse angles, which ends 27, 28 may then substantially parallel the sloping sides of the stem portion 23.

Instead of the solid construction shown, the grapple-like member 20 may be made of heavy flat metal stock whose mid portion is formed to the contour of the stem portion 23 and whose end portions may extend outward from center opposite to each other, to form similar grapple hook portions 25, 27, 26, 28.

In use, as illustrated in FIG. 1, the left knee, which is to be studied, is positioned approximately midway between the table edges *b, c*. Having adjusted the strap loop length so that the grapple hook member 20 may grasp either of these table edges, and secured the complementary VELCRO faces 13, 14 together, the strap loop may be positioned about the femoral condyles immediately above the left knee joint, and drawn beneath the right thigh, with the then lower hook portion 26 drawn over the table edge *b* and engaging it. This will permit study of the medial side of the left knee joint. These joint spaces are widened by having the operator apply, below the limb joint, and preferably at or near the ankle, a force in the direction opposite that of the extension of the loop, as shown in the solid arrow. The operator so applies sufficient stress to permit conventional procedures to study that side of the joint in whose direction the loop extends. Thus if the study is to be a radiographic study, a dye may conventionally be first injected into the knee joint, optionally with air. In applying such stress by the force shown by the solid arrow against the resistance of the strap loop 10, the resultant widening of the spaces at the medial side will effect definition of the femoral and tibial cartilages and the meniscus; and an arthrogram may be made. The stress is then released; and the hook portion 26 is released from the table edge *b*.

Then for studying the opposite side of the joint, the strap loop 10 is drawn from beneath the patient's right leg and the grapple hook member 20 is slipped therealong and its hook portion 25 is engaged over the opposite table edge *c*. This permits studying the lateral side of the joint toward which the strap extends. The operator then applies, as shown in the phantom arrow, a force in the direction opposite to that to which the strap loop extends. By so doing, he applies sufficient medial stress to the joint to permit study of its lateral side. After exposure for the arthrogram, the force is released, and the technologist releases the hook portion 25 and removes the strap member 10.

The procedure for applying stress to the patient's other knee will be obvious.

Regardless which of the hook members 25, 26 is applied, the grapple member 22 is positioned in the same plane *e*, without twisting the strap member 10. All that is required to change from varus to valgus stress is to release the application of force below the knee of the patient, remove the hook portion which is grasping the table edge, slide the grapple member along the strap 10, and reapply its other hook member to the opposite table edge. No twisting force is applied to the strap and there is no discomfort to the patient.

Instead of using the grapple member 20, a grasping member having a single hook portion might be used with swivel means to mount to the loop strap 10. In such embodiment the hook means would be twisted about its swivel, without twisting the loop strap out of the plane *e*.

While the principal use of the apparatus in this method will be for knee arthrography, the same joint stressing procedure is utilized for studies of joint stability, and may be adapted for studying other limb joints, particularly the elbow joint, as will from this disclosure be apparent.

The advantages of the present invention include the following. Both the medial and lateral sides of the joint are studied without removing the strap from around it, or even repositioning the strap, except for drawing it under the other leg when the medial side of a knee is to be studied. Yet the patient remains comfortable partly because the strap is not twisted. The manipulations are simple and quick. The operator works safely out of range of the radiation employed. The strap fits about the thighs of any configuration, regardless how obese they may be; and permits the joint to be positioned elevated from the surface of the fluoroscopic table if required.

Individual arthrographers will have their own personal preferences as to apparatus and procedures. Since the same arthrographer may work at more than one hospital or clinic, he may carry the present apparatus with him; it is light, portable and need not be mounted onto the fluoroscopic table.

From this disclosure, modifications in details of apparatus and the method of its use will be apparent to persons skilled in the art.

I claim:

1. The method of widening the spaces at the medial and lateral sides of a limb joint for studying them alternately, comprising the steps of positioning the limb, whose joint is to be so studied, on a study table with one side so to be studied nearer to one edge of the table and the other side nearer to its other edge, looping a strap having a sliding hook member about the limb above the joint and so adjusting its loop length that the hook member may grasp either table edge, then alternately widening the joint spaces at and studying the medial and the lateral sides of said joint by:

a. extending the strap toward that edge of the table nearer to the side of the joint to be first studied, b. grasping said edge with said hook member, c. applying to the limb below said joint a force in the direction opposite to the extension of the loop, whereby stress is applied sufficient to permit study of that side of the joint in whose direction the loop extends, and then studying said side, d. releasing the force so applied below the joint, and releasing the grasp of the hook member, and then, for studying the opposite side, e. extending the strap loop toward the opposite edge of the table, f. grasping with the hook member the table edge toward the strap loop so extends, g. applying to the limb below said joint a force in the direction opposite that to which the strap loop extends, whereby stress is applied sufficient to permit study of that side of the joint, and after such study releasing the force so applied, releasing the hook member and removing the strap loop.

2. The method of widening joint spaces for study, as defined in claim 1, wherein
   the joint to be studied is a knee, and
   the strap is looped immediately above the femoral condyles.

3. The method as defined in claim 2, wherein
   such widening of the spaces at the medial and lateral sides of the joint separates the femur and tibia.

4. The method as defined in claim 1, wherein
   the study of medial and lateral sides of the joint is a radiographic study, together with the conventional initial steps of
   injecting a radiographic contrast agent,
   whereby such widening of the spaces effects definition of the femoral and tibial cartilages and the menisci.

5. The method as defined in claim 1, wherein
   the study of said medial and lateral sides of the joint is the testing of joint stability by conventional procedures.

6. Apparatus for widening the spaces at the medial and lateral sides of a limb joint for studying them alternately on a study table having side edges, comprising:
   strap means to form an adjustable loop whose length is sufficient to surround such limb when in centered position on such table and to extend toward either side edge thereof, and
   means, slidably mounted on said strap, to grasp either side edge of such table when the loop surrounds such limb and is extended toward that edge,
   said means to grasp including means to avoid twisting said looped strap when extended toward either edge of said table.

7. Apparatus as defined in claim 6, wherein said means to grasp comprises
   a grapple-like member having
   a stem portion and
   two hook portions extending in opposite directions from one end thereof, whereby to define a grapple hook plane, each of said hook portions being of sufficient width to grasp an edge of such table,
   the stem portion having at its opposite end means to mount the looped strap substantially perpendicular to such grapple hook plane.

8. Apparatus as defined in claim 6, wherein said means to grasp comprises
   a hook portion of sufficient width to grasp an edge of such table, said hook portion extending from one end of a stem portion which has at its opposite end swivel means to mount to said looped strap.

* * * * *